(12) United States Patent
Okumura et al.

(10) Patent No.: US 7,415,877 B2
(45) Date of Patent: Aug. 26, 2008

(54) GAS SENSOR

(75) Inventors: Tatsuya Okumura, Kani (JP);
Tomohiro Nakamura, Kounan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 330 days.

(21) Appl. No.: 10/558,236

(22) PCT Filed: Mar. 18, 2005

(86) PCT No.: PCT/JP2005/004913

§ 371 (c)(1),
(2), (4) Date: Nov. 23, 2005

(87) PCT Pub. No.: WO2005/090960

PCT Pub. Date: Sep. 29, 2005

(65) Prior Publication Data

US 2006/0288759 A1    Dec. 28, 2006

(30) Foreign Application Priority Data

Mar. 19, 2004    (JP)    ............................. 2004-079813

(51) Int. Cl.
*G01D 11/10*    (2006.01)
*G01D 11/24*    (2006.01)
(52) U.S. Cl. .................. 73/431; 73/29.05; 73/31.05
(58) Field of Classification Search ................ 73/24.06, 73/25.05, 29.05, 30.01–31.07, 431
See application file for complete search history.

(56) References Cited

U.S. PATENT DOCUMENTS 4,439,911 A * 4/1984 Ikezawa et al. ............ 29/25.03
4,818,363 A * 4/1989 Bayha et al. ................ 204/426
5,039,972 A * 8/1991 Kato et al. ................... 338/34
5,246,562 A * 9/1993 Weyl et al. .................. 204/424

(Continued)

FOREIGN PATENT DOCUMENTS

JP    58027052 A  *  2/1983

(Continued)

*Primary Examiner*—David A. Rogers
(74) *Attorney, Agent, or Firm*—Sughrue Mion, PLLC

(57) ABSTRACT

To provide a gas sensor in which connection terminals are stably brought into contact with electrode terminal portions of a sensor element without superfluous load applied on the sensor element. A pair of element guide portions 33 are provided in a sleeve 30 in which a plate-like sensor element 10 is inserted. The pair of element guide portions 33 protrude from an opening end surface on a rear end side of an axial hole 31, store either of widthwise opposite side ends of the sensor element 10 and restrain the sensor element 10 from being inclined. The sensor element 10 is positioned coaxially with the sleeve 30 by the element guide portions 33. Electrode holders 40 in which electrode fitments 60 are held are fitted to the element guide portions 33 so that the electrode fitments 60 are brought into contact with electrode terminal portions 15 and 16 of the sensor element 10. Because the positional relation between the two is decided on the basis of the element guide portions 33, there is no superfluous load applied on the sensor element 10, so that the sensor element 10 is prevented from being broken. In addition, pressure of contact of the electrode fitments 60 with the electrode terminal portions 15 and 16 of the sensor element 10 is kept substantially constant, so that electrically stable connection can be obtained.

10 Claims, 11 Drawing Sheets

U.S. PATENT DOCUMENTS

| | | | | |
|---|---|---|---|---|
| 5,627,306 | A | * | 5/1997 | Yamauchi et al. ............ 73/23.2 |
| 5,846,391 | A | * | 12/1998 | Friese et al. ................. 204/424 |
| 6,206,377 | B1 | * | 3/2001 | Weyl ........................... 277/317 |
| 6,254,749 | B1 | * | 7/2001 | Yokota et al. ................ 204/424 |
| 6,474,655 | B1 | * | 11/2002 | Weyl et al. ................... 277/650 |
| 6,672,132 | B1 | * | 1/2004 | Weyl et al. .................. 73/23.31 |
| 6,688,157 | B2 | * | 2/2004 | Yamada et al. ................ 73/23.2 |
| 6,708,551 | B2 | * | 3/2004 | Kojima ....................... 73/31.05 |
| 6,878,252 | B2 | * | 4/2005 | Weyl et al. ................... 204/424 |
| 7,197,912 | B1 | * | 4/2007 | Duce et al. ................. 73/31.05 |
| 2002/0148280 | A1 | * | 10/2002 | Weyl et al. .................. 73/31.05 |
| 2003/0024300 | A1 | | 2/2003 | Kojima |
| 2004/0040843 | A1 | * | 3/2004 | Weyl et al. ................... 204/424 |

FOREIGN PATENT DOCUMENTS

| | | | | |
|---|---|---|---|---|
| JP | 02190757 | A | * | 7/1990 |
| JP | 04295750 | A | * | 10/1992 |
| JP | 10253578 | A | * | 9/1998 |
| JP | 2002131269 | A | * | 5/2002 |
| JP | 2002-168822 | A | | 6/2002 |
| JP | 2002-296223 | A | | 10/2002 |
| JP | 2002-323475 | A | | 11/2002 |
| JP | 2003-43004 | A | | 2/2003 |
| JP | 2003043003 | A | * | 2/2003 |
| WO | WO 2004017058 | A1 | * | 2/2004 |

* cited by examiner

GAS SENSOR

TECHNICAL FIELD

The present invention relates to a gas sensor having a built-in sensor element for detecting a specific gas component in exhaust gas discharged from an internal combustion engine.

BACKGROUND ART

There is heretofore known a gas sensor having a sensor element for detecting a specific gas component in exhaust gas of a car or the like. The sensor element of such a gas sensor is formed as a plate-like element having at least one layer of solid electrolyte clamped between a pair of electrodes and detects the concentration of a specific gas (e.g. oxygen) in exhaust gas. Because the solid electrolyte is not activated when the temperature is low, a heater for heating the sensor element to activate it is generally provided near the sensor element. For example, a product having a laminate structure in which a plate-like heater and a sensor element are baked so as to be integrated with each other is known as a heater integral type senor element.

In the condition that such a sensor element is inserted into an axial hole of a ceramic sleeve (element side electrical porcelain), the sensor element is glass-sealed to thereby be held in the sleeve. The sleeve is held in a metal shell so that the sensor element can be finally incorporated in the metal shell. To take an output from the sensor element, an electrode holder (atmospheric air side electrical porcelain) is put so that electrode terminal portions provided on upper and lower surfaces respectively on the rear end side of the sensor element are covered with the electrode holder. Connection terminals are provided in the electrode holder so that the connection terminals abut on the electrode terminal portions of the sensor element. When the sensor element and electrode springs are clamped from opposite surfaces of the sensor element, electrical connection between the electrode terminal portions and the connection terminals can be ensured.

If the electrode holder and the sleeve are fitted to each other on this occasion, the two are aligned with each other so that the electrode holder is prevented from being disposed so as to be inclined with respect to the sleeve. For this reason, the rear end portion of the sensor element inserted in the electrode holder is prevented from being broken by collision with the inner surface of the electrode holder (e.g. see Patent Document 1).

Patent Document 1: Japanese Patent Laid-Open No. 2003-43004

DISCLOSURE OF THE INVENTION

Problem that the Invention is to Solve

In the gas sensor described in Patent Document 1, the electrode holder is however positioned coaxially with the sleeve, not the sensor element. For this reason, when the sensor element inserted in the axial hole is held in the sleeve while inclined, superfluous load is applied on the sensor element at the time of assembling the electrode holder so that there arises a problem that the sensor element is broken at the time of assembling. In this case, there is a possibility that electrical connection to the electrode terminal portions will become unstable because one plate surface (upper surface) of the sensor element is different from the other plate surface (lower surface) thereof in contact pressure from the connection terminals.

The invention is accomplished to solve the aforementioned problem and an object of the invention is to provide a highly reliable gas sensor in which connection terminals can be stably brought into contact with electrode terminal portions of a sensor element without superfluous load applied on the sensor element.

Means for Solving the Problem

To achieve the foregoing object, the gas sensor according to a first invention is a gas sensor including a cylindrical metal shell, a plate-like sensor element extending in a lengthwise direction, and a sleeve held in the inside of the metal shell, the plate-like sensor element including a front end side exposed to gas to be measured, and electrode terminal portions formed on a rear end side so as to come into contact with connection terminals, the sleeve including an axial hole in which the sensor element is inserted, said gas sensor being characterized in that the sleeve further includes element guide portions which protrude from an opening end surface on a rear end side of the axial hole and which restrain the sensor element from being inclined in a direction crossing the axial direction of the axial hole.

According to the gas sensor of the invention, the element guide portions are provided in the sleeve in which the sensor element is inserted. The element guide portions protrude from an opening end surface on a rear end side of the axial hole and restrain the sensor element from being inclined in a direction crossing the axial direction of the axial hole. While the sensor element can be inserted in the axial hole of the sleeve by the element guide portions, the sensor element having the rear end side protruding from the opening end surface on the rear end side of the axial hole can be prevented from being disposed so as to be inclined in a direction crossing the axial direction of the axial hole.

Accordingly, even in the case where a member in which the connection terminals brought into contact with the electrode terminal portions of the sensor element are disposed in the inside is disposed coaxially with the sleeve, superfluous load can be restrained from being applied on the sensor element, so that damage of the sensor element such as breaking of the element can be prevented. Even when the connection terminals are brought into contact with the electrode terminal portions formed on upper and lower surfaces of the sensor element respectively, contact pressure from the connection terminals is kept substantially constant in the upper and lower surfaces of the sensor element. For this reason, the connection terminals can be stably brought into contact with the electrode terminal portions of the sensor element, so that respective electrical connection can be made good.

Preferably, in the gas sensor, the sleeve may include a pair of element guide portions which are arranged opposite to each other with respect to the center axial line of the axial hole.

When a pair of element guide portions are provided opposite to each other with respect to the center axial line of the axial hole as described above, the sensor element can be disposed stably coaxially with the sleeve (in detail, the axial hole of the sleeve).

Preferably, in the gas sensor, the pair of element guide portions may have groove portions continued to the inner circumference of the axial hole so that either of widthwise opposite side ends of the sensor element is stored in the groove portions.

When groove portions continued to the inner circumference of the axial hole are provided in each of the pair of element guides so that either of the widthwise opposite side ends of the sensor element is stored in the groove portions, both inclination of the sensor element in the direction of the width and inclination of the sensor element in the direction of the thickness can be prevented surely. Accordingly, the sensor element can be disposed stably coaxially with the sleeve (in detail, the axial hole of the sleeve), so that a more highly reliable gas sensor can be provided.

Preferably, in the gas sensor, while insulation holding members are arranged around the rear end side of the sensor element, the connection terminals may be arranged between the sensor element and the insulation holding members so as to come into contact with the electrode terminal portions; and inner surfaces of the insulation holding members are fitted to outer surfaces of the element guide portions.

According to the gas sensor of the invention, inner surfaces of the insulation holding members disposed around the rear end side of the sensor element in the condition that the connection terminals are disposed in the inside are fitted to outer surfaces of the element guides. Accordingly, because the element guide portions are interposed between the rear end side of the sensor element and the insulation holding members, the inner surfaces of the insulation holding members can be prevented from colliding with the circumferential surface on the rear end side of the sensor element at the time of assembling or when the gas sensor in use is attached to a portion on which vibration is intensively applied (such as an exhaust pipe of a car). The sensor element can be surely prevented from being broken.

In addition, because the insulation holding members are prevented from being disposed so as to be inclined with respect to the element guides, pressure of contact of the respective connection terminals with the electrode terminal portions of the sensor element can be set to be more uniform. Accordingly, the connection terminals can be brought into contact with the electrode terminal portions of the sensor element more stably, so that a more highly reliable gas sensor can be provided.

Preferably, in the gas sensor, the insulation holding members may make a pair and clamp and fix the connection terminals and the sensor element. When the connection terminals and the sensor element are clamped and fixed by use of the insulation holding members making a pair in this manner, the connection terminals can be surely brought into contact with the electrode terminal portions of the sensor element.

Preferably, the gas sensor according to this aspect may further include: a protection cover fixed to the metal shell so as to surround the insulation holding members; and a retaining fitment which is shaped like a pipe surrounding the outer circumferences of the insulation holding members and which is held in the inside of the protection cover while the connection terminals and the sensor element are kept clamped by the insulation holding members. Accordingly, even in the case where vibration reaches the gas sensor, the insulation holding members making a pair can be held stably. Even when external impact caused by scattering stone or the like is applied on the protection cover, the impact applied on the insulation holding members can be relaxed by the retaining fitment. Accordingly, because stress transmitted to the sensor element can be reduced, the sensor element can be effectively prevented from being broken.

Preferably, in the gas sensor, the insulation holding members may be replaced by a single member which is provided for covering the rear end side surroundings of the sensor element and which has though-holes on the rear end side so that lead wires connected to the connection terminals are inserted in the through-holes. When the insulation holding member made of a single member is disposed so as to be put on the rear end side of the sensor element as described above, the connection terminals can be surely brought into contact with the electrode terminal portions of the sensor element while the connection terminals are clamped between the inner surface of the insulation holding member and the sensor element. When insertion holes are provided in the insulation holding member so that lead wires connected to the connection terminals can be inserted in the insertion holes respectively, the lead wires can be prevented from being entangled with one another at the time of assembling the gas sensor, so that short-circuiting can be prevented from occurring.

Preferably, the gas sensor according to this aspect may further include: a protection cover fixed to the metal shell so as to surround the insulation holding member; and a retaining fitment which is held in the inside of the protection cover while the insulation holding member is held in the inside of the retaining fitment. Accordingly, even in the case where vibration reaches the gas sensor, the insulation holding members making a pair can be held stably. Even when external impact caused by scattering stone or the like is further applied on the protection cover, the impact applied in the insulation holding members can be relaxed by the retaining fitment. Accordingly, because stress transmitted to the sensor element can be reduced, the sensor element can be effectively prevented from being broken.

To achieve the foregoing object, the gas sensor according to a second invention is a gas sensor including a cylindrical metal shell, a plate-like sensor element extending in a lengthwise direction, and a sleeve held in the inside of the metal shell, the plate-like sensor element including a front end side exposed to gas to be measured, and electrode terminal portions formed on a rear end side so as to come into contact with connection terminals, the sleeve including an axial hole in which the sensor element is inserted, the gas sensor being characterized in that the sleeve further includes element guide portions which protrude from an opening end surface on a rear end side of the axial hole and which guide the rear end side of the sensor element coaxially with the axial hole.

According to the gas sensor of the invention, the element guide portions are provided in the sleeve in which the sensor element is inserted. The element guide portions protrude from an opening end surface on a rear end side of the axial hole and guide the rear end side of the sensor element coaxially with the axial hole. Accordingly, when the sensor element is inserted in the axial hole of the sleeve, the rear end side of the sensor element can be guided by the element guide portions. The sensor element can be disposed (positioned) coaxially with the axial hole of the sleeve. Accordingly, the sensor element can be prevented from being inclined in a direction crossing the axial direction of the axial hole.

Accordingly, even in the case where a member in which the connection terminals brought into contact with the electrode terminal portions of the sensor element are disposed in the inside is disposed coaxially with the sleeve, superfluous load can be restrained from being applied on the sensor element, so that damage of the sensor element such as breaking of the element can be prevented. Even when the connection terminals are brought into contact with the electrode terminal portions formed on upper and lower surfaces of the sensor element respectively while the connection terminals are pressed against the electrode terminal portions, contact pressure from the connection terminals is kept substantially constant in the upper and lower surfaces of the sensor element. For this reason, the connection terminals can be stably brought into contact with the electrode terminal portions of the sensor element, so that respective electrical connection can be made good.

DESCRIPTION OF REFERENCE NUMERALS

Figure 1:
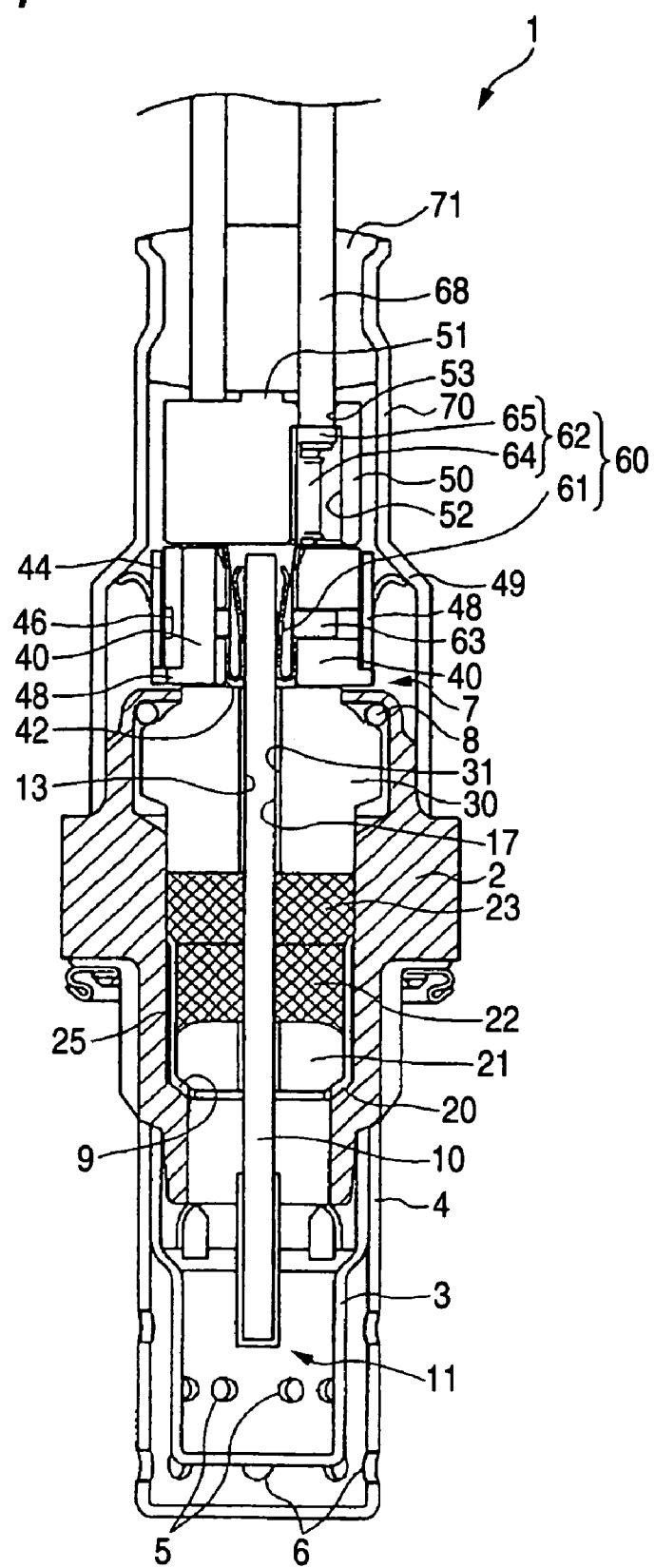
[FIG. 1] A cutaway sectional view of a main portion of a gas sensor 1 according to an embodiment.

1 . . . gas sensor
2 . . . metal shell
10 . . . sensor element
15, 16 . . . electrode terminal portion
30 . . . sleeve
31 . . . axial hole
33 . . . element guide portion
35 . . . groove portion
40, 140, 240 . . . electrode holder (insulation holding member)
48 . . . retaining fitment
49 . . . protrusion portion
50 . . . separator
52 . . . insertion hole
53 . . . small diameter portion
60 . . . electrode fitment (connection terminal)
68 . . . lead wire
70 . . . protection cover

BEST MODE FOR CARRYING OUT THE INVENTION

Figure 2:
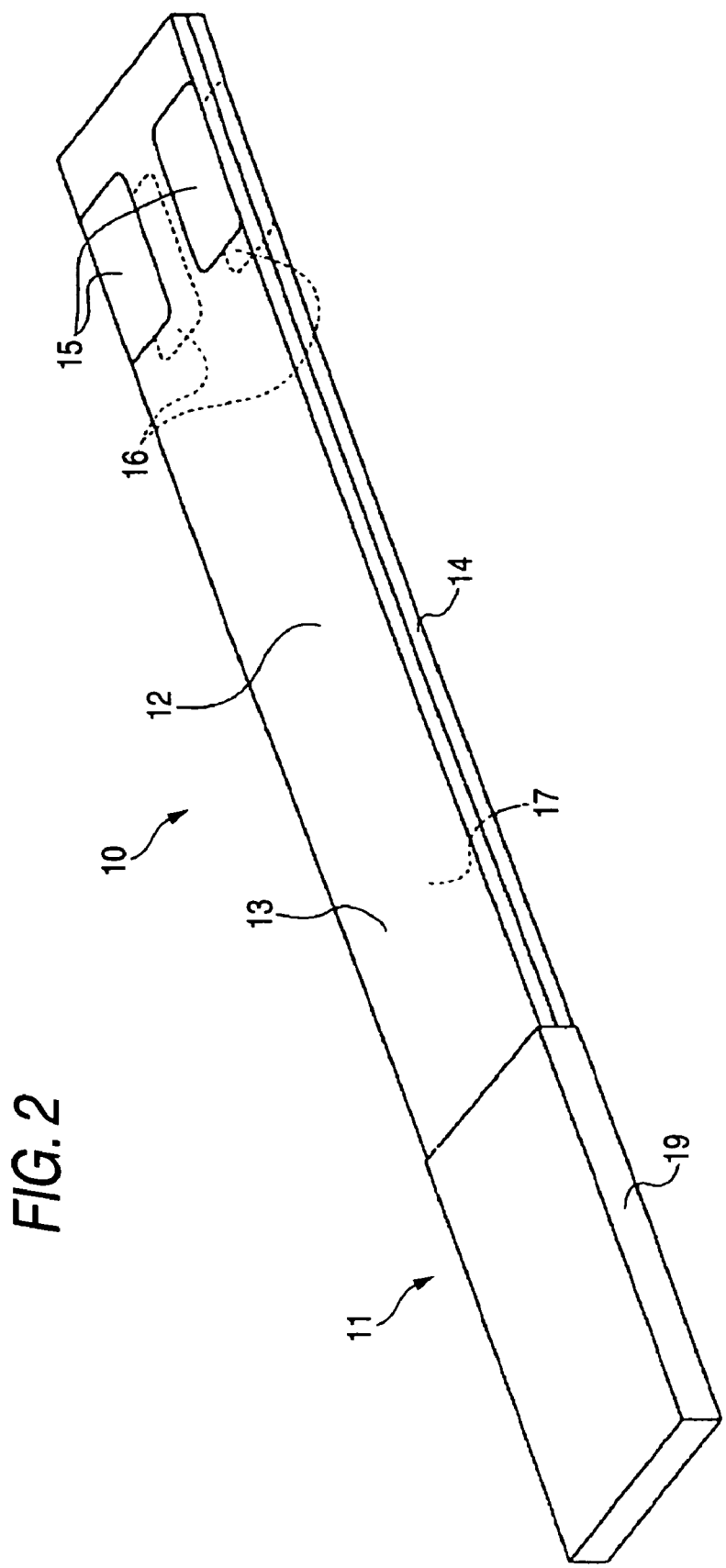
[FIG. 2] A perspective view showing schematic configuration of a sensor element 10.
Figure 3:
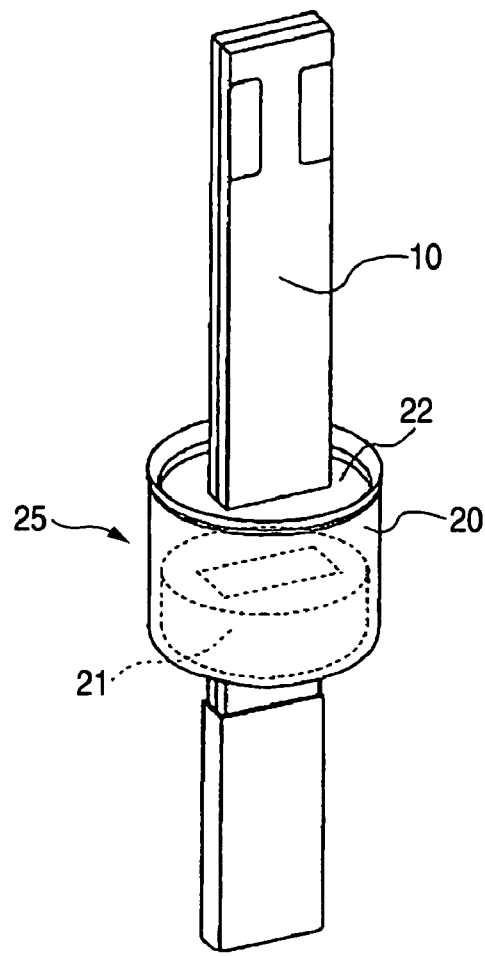
[FIG. 3] A perspective view showing a state in which a flange portion 25 fitted to a metal shell 2 is integrally combined with the sensor element 10.
Figure 4:
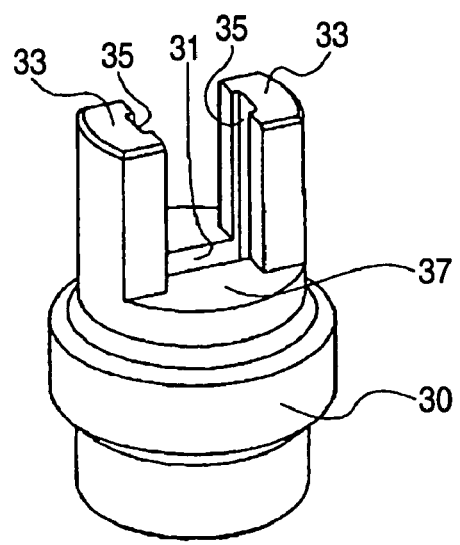
[FIG. 4] A perspective view of a sleeve 30 having element guide portions 33.
Figure 5:
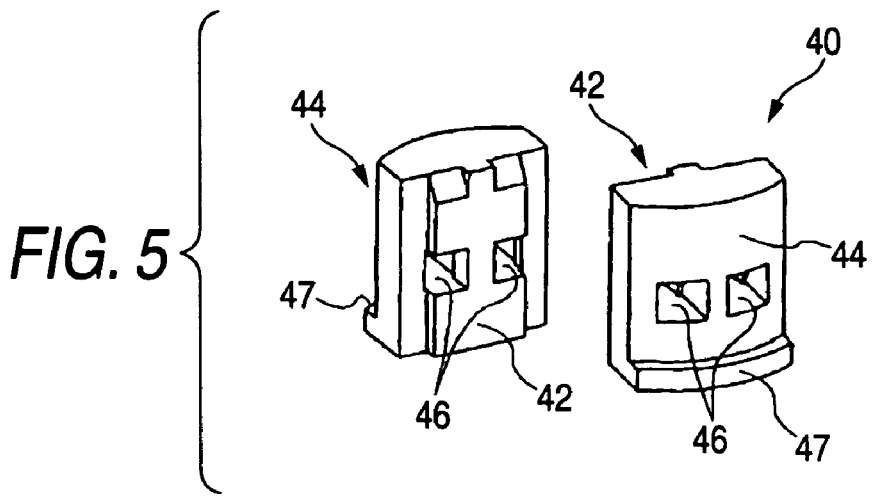
[FIG. 5] A perspective view of electrode holders 40.
Figure 6:
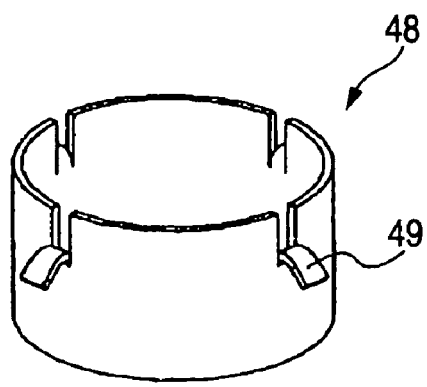
[FIG. 6] A perspective view of a retaining fitment 48.
Figure 7:
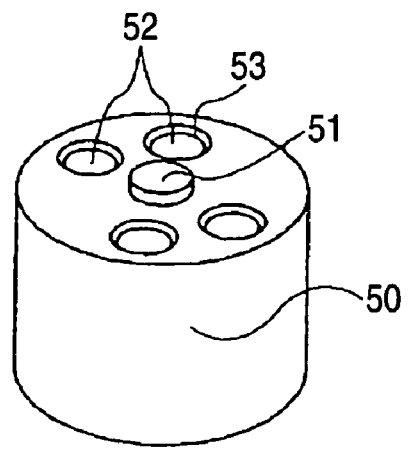
[FIG. 7] A perspective view of a separator 50.
Figure 8:
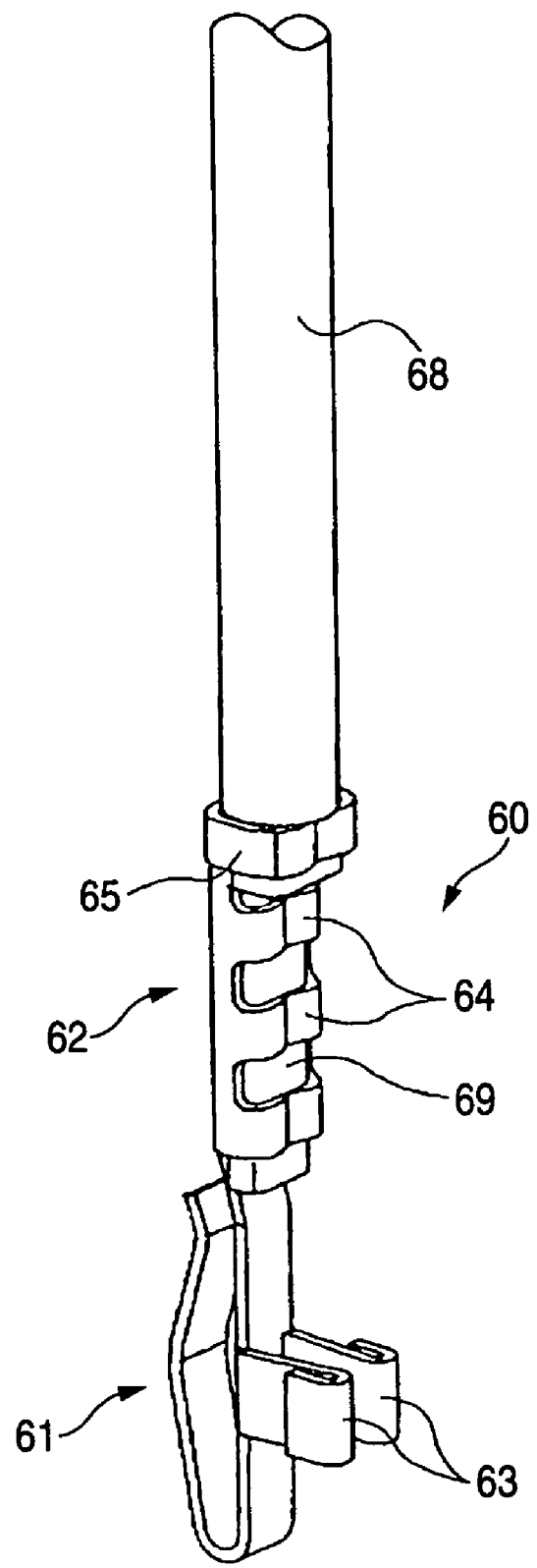
[FIG. 8] A perspective view of an electrode fitment 60 in which a lead wire 68 is caulked.

A gas sensor 1 according to an embodiment of the invention will be described below with reference to the drawings. Referring first to FIGS. 1 through 8, the schematic structure of the gas sensor 1 will be described. FIG. 1 is a cutaway sectional view of a main portion of the gas sensor 1. FIG. 2 is a perspective view showing the schematic configuration of a sensor element 10. FIG. 3 is a perspective view showing a state in which a flange portion 25 to be fitted into a metal shell 2 is integrally combined with the sensor element 10. FIG. 4 is a perspective view of a sleeve 30. FIG. 5 is a perspective view of an electrode holder 40. FIG. 6 is a perspective view of a retaining fitment 48. FIG. 7 is a perspective view of a separator 50. FIG. 8 is a perspective view of an electrode fitment 60 by which a lead wire is caulked. Incidentally, description will be made below on the assumption that a direction on the detection portion 11 side of the sensor element 10 in the axial direction of the gas sensor 1 (vertical direction of the paper surface in FIG. 1) when respective members are incorporated in the gas sensor 1 is regarded as a front end side while a side located opposite to the detection portion 11 side of the sensor element 10 is regarded as a rear end side.

The gas sensor 1 shown in FIG. 1 is an oxygen sensor which is mounted in an exhaust pipe of a car in use and which is provided for detecting the concentration of oxygen in exhaust gas flowing in the exhaust pipe. The plate-like sensor element 10 is held in the metal shell 2 in the condition that a front end portion (detection portion 11) of the sensor element 10 protrudes from a front end of the metal shell 2. As shown in FIG. 2, the sensor element 10 in this embodiment is formed so that a plate-like element portion 12 extending in the axial direction and a plate-like heater 14 likewise extending in the axial direction are laminated. The element portion 12 and the heater 14 are baked so as to be integrated with each other. The element portion 12 is provided in such a manner that a pair of porous electrodes (detection electrode and reference electrode) mainly containing platinum are formed on opposite surfaces of a solid electrolyte board mainly containing zirconia in which yttria is solid-dissolved as a stabilizer. The heater 14 is formed in such a manner that a heating resistor mainly containing platinum is sandwiched between electrically insulating boards mainly containing alumina.

In this sensor element 10, a detection portion 11 in which the porous detection electrode and the porous reference electrode (not shown) are arranged is provided on the front end side of the element portion 12 in the lengthwise direction whereas two electrode terminal portions 15 electrically connected to the detection electrode and the reference electrode respectively are provided on a first plate surface (upper surface) 13 on the rear end side. Two electrode terminal portions 16 serving as positive and negative electrodes for applying a voltage to the heating resistor (not shown) are formed on a second plate surface (lower surface) 17 on the rear end side of the sensor element 10. An electrode protection layer 19 made of an antitoxic porous ceramic is formed at least on a upper surface of the electrode (detection electrode) exposed to exhaust gas on the front end side of the sensor element 10. Incidentally, in this embodiment, a front end side circumferential surface including the upper surface of the electrode exposed to exhaust gas in the sensor element 10 is covered with the electrode protection layer 19.

Next, as shown in FIGS. 1 and 3, the flange portion 25 integrally combined with the sensor element 10 has a ceramic ring 21 of alumina, a talc ring 22 filled with compressed talc powder, and a metal holder 20 shaped like a pipe with a size enough to store the ceramic ring 21 and the talc ring 22 in the inside. Incidentally, the flange portion 25 is combined with the sensor element 10 as follows. First, the talc ring 22 having an opening sectional area through which the sensor element 10 can pass is prepared. The metal holder 20, the ceramic ring 21 and the talc ring 22 are arranged successively in predetermined positions of the sensor element 10. Pressure to reduce the opening sectional area of the through-hole of the talc ring 22 is given to compressively deform the talc ring 22 to thereby integrally combine the metal holder 20 and the ceramic ring 21 as well as the talc ring 22 with the sensor element 10. As a result, the flange portion 25 to be fitted to a step portion 9 of the metal shell 2 is provided while fixed to the sensor element 10.

As shown in FIG. 1, the step portion 9 formed to have an inner diameter reduced is provided on the front end side (lower side in FIG. 1) of the metal shell 2. The outer diameter of the flange portion 25 is formed to be substantially equal to the inner diameter of the metal shell 2. When the flange portion 25 is inserted into the metal shell 2 so that the front end portion of the flange portion 25 abuts on the step portion 9, the flange portion 25 is positioned relative to the metal shell 2. In the metal shell 2 into which the flange portion 25 (metal holder 20) is fitted, the rear end side (upper layer in FIG. 1) of the metal holder 20 is compressively filled with the talc ring 23. As a result, while the flange portion 25 is fixed into the metal shell 2, the sensor element 10 is positioned and fixed relative to the metal shell 2. Incidentally, compression of the talc ring 23 is performed in such a manner that a sleeve 30 which will be described later presses the talc ring 23 when the sleeve 30 is incorporated in the metal shell 2.

The detection portion 11 of the sensor element 10 is exposed out of the metal shell 2 on the front end side (lower side in FIG. 1) of the gas sensor 1. A bottomed cylindrical inner protector 3 for covering and protecting the detection portion 11 and an outer protector 4 for covering the inner protector 3 are fixed to the metal shell 2 by laser welding. A plurality of outside air communication holes 5 (6) are formed in each of the inner protector 3 and the outer protector 4 so that the detection portion 11 of the sensor element 10 is exposed to the atmosphere (exhaust gas) around the gas sensor 1.

Next, a multistage cylindrical sleeve 30 of aluminum is provided on the rear end side of the gas sensor 1 with respect to the talc ring 23. The sleeve 30 as well as the flange portion 25 is stored in the metal shell 2 while the sleeve 30 presses the talc ring 23 toward the front end side. As shown in FIGS. 1 and 4, the sleeve 30 has an axial hole 31 in its axial direction. The sensor element 10 is inserted into the axial hole 31. The axial hole 31 is formed so that the area (opening area) of a section in the axial direction is slightly larger than the area of a section in the lengthwise direction of the sensor element 10. In the condition that the sleeve 30 is stored in the metal shell 2, the respective electrode terminal portions 15 and 16 of the sensor element 10 are exposed out of the caulking portion 7 side of the metal shell 2.

As shown in FIG. 4, the sleeve 30 has a pair of element guide portions 33 provided so as to protrude. The pair of element guide portions 33 extend from an opening end surface 37 on the rear end side of the axial hole 31 toward the rear end (upward in FIG. 4) along the axial direction (axial hole 31) of the sleeve 30. The pair of element guide portions 33 are arranged opposite to each other with respect to the center axial line of the axial hole 31. Each element guide portion 33 has a groove portion 35 continuously provided in the inner circumference of the axial hole 31 in order to store and guide either of widthwise opposite side ends on the rear end side of the sensor element 10. The length of the groove portion 35 is decided so that the sensor element 10 does not project when the sleeve 30 is incorporated. The depth of the groove portion 35 is decided so that at least part of the electrode terminal portions 15 and 16 of the sensor element 10 can be exposed when either of the widthwise opposite side ends of the sensor element 10 is stored in the groove portion 35. The electrode terminal portions 15 and 16 are partially exposed by areas necessary for the electrode fitment 60 (which will be described later) to come into contact with the electrode terminal portions 15 and 16. The width of the groove portion 35 is formed to be slightly larger than the thickness of the sensor element 10. Incidentally, the electrode fitment 60 is equivalent to the "connection terminal" in the scope of claim for this invention.

As shown in FIG. 1, when the caulking portion 7 of the metal shell 2 is bent inward so as to be caulked, the sleeve 30 is pressed toward the front end side of the metal shell 2 through a stainless steel ring member 8 interposed in the inside. As a result, the talc ring 23 is compressively deformed to fill in the surrounding gap, so that the sensor element 10 is held and fixed in the metal shell 2 gastightly.

Next, the first plate surface 13 and the second plate surface 17 on which the respective electrode terminal portions 15 and 16 of the sensor element 10 protruding from the rear end of the metal shell 2 are formed are clamped by a pair of electrode holders 40 through the electrode fitment 60 from opposite sides in the direction of the thickness of the sensor element 10. As shown in FIGS. 1 and 5, the electrode holders 40 are formed so that the inner surfaces of the electrode holders 40 are fitted to the outer surfaces of the element guide portions 33 (see FIG. 4) of the sleeve 30. Each electrode holder 40 has an inner wall surface 42 facing the sensor element 10 guided (stored) by the element guide portion 33, and an outer wall surface 44 for forming an outer circumferential surface which is curved so that a section in the axial direction as formed together with the element guide portion 33 is substantially circular. A flange portion 47 is formed near the front end of the outer wall surface 44. Incidentally, the electrode holders 40 are equivalent to the "insulation holding members" in the scope of claim for this invention.

Each of the pair of electrode holders 40 has two openings 46 substantially provided in the center in the axial direction so as to pass through between the inner wall surface 42 and the outer wall surface 44. Projection pieces 63 (see FIG. 8) of the electrode fitments 60 (which will be described later) are fitted to inner surfaces of the openings 46, so that the electrode fitments 60 are positioned in predetermined positions on the inside of the electrode holders 40. In this embodiment, two electrode fitments 60 are fitted to each electrode holder 40 to perform electrical connection to positive and negative electrodes of the electrode terminal portion 15 provided on the first plate surface 13 of the sensor element 10 and the electrode terminal portion 16 provided on the second plate surface 17 of the sensor element 10.

When the electrode holders 40 are engaged with the element guide portions 33 in the condition that the electrode fitments 60 are held in the inside of the electrode holders 40, a retaining fitment 48 is fitted to the outer wall surfaces 44 of the pair of electrode holders 40 in order to keep the engagement (see FIG. 1). As shown in FIG. 6, the retaining fitment 48 is shaped like a pipe and has notches so that two notches are adjacently provided in the axial direction at each pipe end, that is, notches are provided in four directions with respect to the axial direction. A region located between the adjacent two notches is formed as a protrusion portion 49. Each protrusion portion 49 is bent so as to be opened to the outside of the retaining fitment 48.

As shown in FIG. 1, in the condition that the retaining fitment 48 is fitted to the electrode holders 40, the electrode fitments 60 clamped between the inner wall surfaces 42 of the electrode holders 40 and the sensor element 10 are distorted. The retaining fitment 48 is however prevented from dropping out because the electrode fitments 60 press the electrode holders 40 against the inner circumference of the retaining fitment 48 by the elastic restoring force of the electrode fitments 60.

Next, as shown in FIG. 1, a separator 50 of alumina for guiding four lead wires 68 to the electrode fitments 60 to electrically connect the sensor element 10 to an external circuit is disposed on the rear end side (upper side in FIG. 1) of the gas sensor 1 with respect to the electrode holders 40. The separator 50 abuts on the rear end surfaces of the electrode holders 40. As shown in FIG. 7, the separator 50 is substantially shaped like a column and has a columnar small protrusion 51 substantially provided in the center of the rear end side surface (upper surface in FIG. 7). Through-holes 52 in the axial direction are provided at four places around the small protrusion 51. As shown in FIG. 1, each through-hole 52 has a small diameter portion 53 which is formed in such a manner that the diameter of a portion on the side of provision of the small protrusion 51 (upper side in FIG. 1) is reduced. The inner diameter of each small diameter portion 53 is substantially equal to the thickness of a corresponding lead wire 68.

As shown in FIG. 1, base portions 62 of the electrode fitments 60 are stored in the through-holes 52. As shown in FIG. 8, the base portions 62 of the electrode fitments 60 are portions for caulking the lead wires 68 to fix the lead wires 68 to the electrode fitments 60. Each base portion 62 has a caulking portion 65 in which the outer circumference of an electrically insulating film with which a conductor wire 69 of the lead wire 68 is coated is caulked to prevent the lead wire 68 from dropping out, and caulking portions 64 in which the conductor wire (stranded wire) 69 in the lead wire 68 is caulked to perform electrical connection. The caulking portion 65 for caulking the outer circumference of the lead wire 68 is formed so as to be larger than the caulking portions 64 for caulking the conductor wire 69. For this reason, as shown in FIG. 1, the diameter of the caulking portion 65 becomes larger than the diameter of the lead wire 68 when the lead wire 68 is caulked. Accordingly, the diameter of the caulking portion 65 becomes larger than the inner diameter of the small diameter portion 53 located on the rear end side of the through-hole 52 of the separator 50, so that the caulking portion 65 cannot pass through the small diameter portion 53.

As shown in FIG. 8, a front end portion 61 of the electrode fitment 60 connected to the base portion 62 is a portion which comes into contact with the electrode terminal portion 15 (16) of the sensor element 10 to perform electrical connection. The front end portion 61 is shaped like a U-shaped spring. Protrusion pieces 63 engaged with one of the openings 46 of the electrode holder 40 to perform positioning to the electrode holder 40 are substantially provided in the center of the front end portion 61 so as to protrude.

Referring back to FIG. 1, an approximately cylindrical protection cover 70 of stainless steel for covering and protecting the electrode holders 40 and the separator 50 is fixed to the outer circumference of the caulking portion 7 of the metal shell 2. In the condition that a stopper member 71 of fluoro rubber is fitted into the rear end portion (on a side opposite to the side fixed to the metal shell 2) of the protection cover 70, the protection cover 70 located in the axial circumference of the stopper member 71 in which only the lead wires 68 are inserted is caulked inward to thereby fix the stopper member 71 into the protection cover 70 in the condition that the stopper member 71 is elastically deformed. The protrusion portions 49 provided on the retaining fitment 48 for the electrode holders 40 abut on the inner wall of the protection cover 70. Because the protrusion portions 49 are provided to protrude in four directions as described above, the retaining fitment 48 per se is held in the protection cover 70 by the elastic force of the protrusion portions 49.

Figure 9:
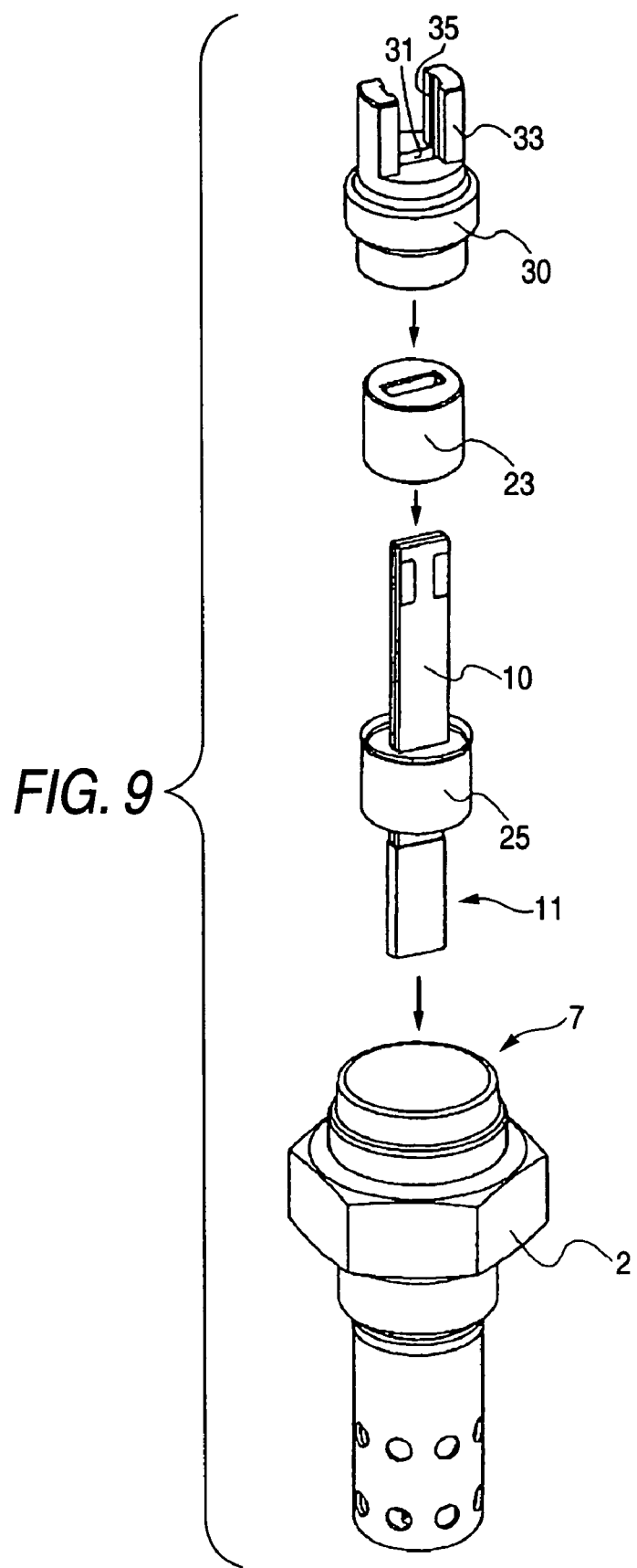
[FIG. 9] An exploded perspective view for explaining combination of the sensor element 10 with the metal shell 2.
Figure 10:
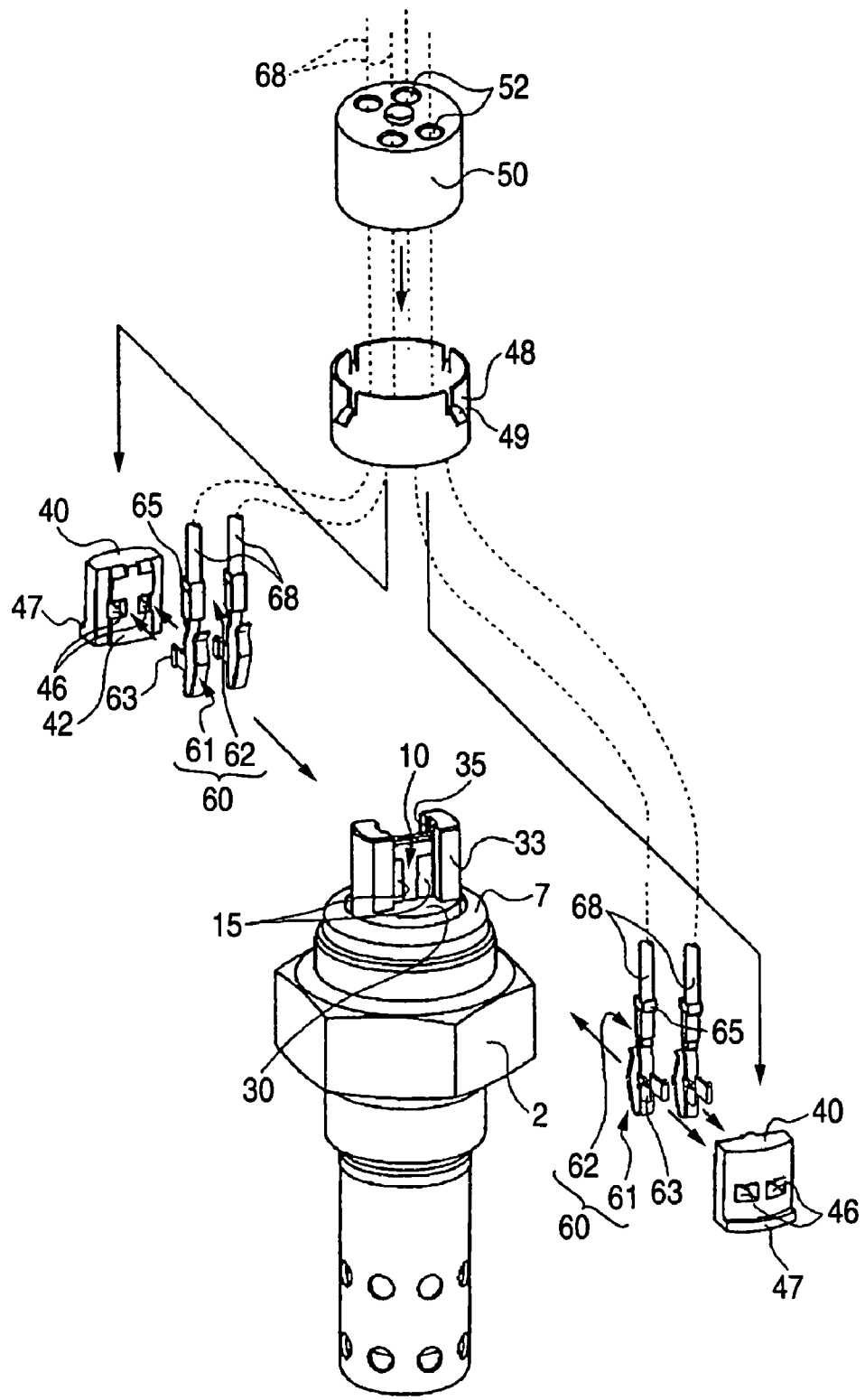
[FIG. 10] An exploded perspective view for explaining combination of the electrode holders 40 with the sensor element 10.

Combining the sensor element 10 with the gas sensor 1 configured as described above will be described with reference to FIGS. 1, 9 and 10. FIG. 9 is an exploded perspective view for explaining combination of the sensor element 10 with the metal shell 2. FIG. 10 is an exploded perspective view for explaining combination of the electrode holders 40 with the sensor element 10.

As shown in FIGS. 1 and 9, the sensor element 10 with which the flange portion 25 is integrally combined is inserted into the metal shell 2 while the detection portion 11 side of the sensor element 10 is provided on the front end side of the metal shell 2. The sensor element 10 is positioned relative to the metal shell 2 in the position where an end portion of the flange portion 25 abuts on the step portion 9 on the front end side (lower side in FIG. 1) of the metal shell 2.

Then, the talc ring 23 is fitted so that the sensor element 10 passes through the center hole of the talc ring 23. Then, the sensor element 10 is inserted in the axial hole 31 of the sleeve 30 from the rear end side of the sensor element 10. On this occasion, the widthwise opposite side ends of the sensor element 10 are guided by the groove portions 35 of the element guide portions 33 continued to the inner circumference of the axial hole 31. Incidentally, although part of the electrode terminal portions 15 and 16 of the sensor element 10 are located in the groove portions 35 of the element guide portions 33, at least part of the electrode terminal portions 15 and 16 are exposed so that connection to the electrode fitments 60 can be performed. When the sensor element 10 is guided by the element guide portions 33 (in detail, the groove portions 35) in this manner, the sensor element 10 can be arranged (positioned) coaxially with the axial hole 31 of the sleeve 30.

In this condition, the ring member 8 is placed on the sleeve 30 and the rear end portion of the metal shell 2 is caulked radially inward to thereby form the caulking portion 7. Because the caulking portion 7 is formed, pressing force toward the front end of the metal shell 2 is applied on the sleeve 30 through the ring member 8 to thereby compress the talc ring 23. The talc ring 23 is deformed to fill in the surrounding gap to thereby fix the flange portion 25 into the metal shell 2.

FIG. 10 shows the state of the metal shell 2 and the sensor element 10 after the formation of the caulking portion 7. The sensor element 10 is fixed into the metal shell 2 while the widthwise opposite side ends of the sensor element 10 are guided by the element guide portions 33.

As shown in FIG. 10, when the protrusion pieces 63 of the electrode fitments 60 are fitted into the openings 46 of the electrode holders 40, the electrode fitments 60 are positioned and held in the electrode holders 40. In this condition, the electrode holders 40 are fitted to the element guide portions 33 while the sensor element 10 is clamped from opposite sides in the direction of the thickness of the sensor element 10. The front end portions 61 of the electrode fitments 60 clamped between the inner wall surfaces 42 of the electrode holders 42 and the plate surfaces of the sensor element 10 abut on the electrode terminal portions 15 and 16 of the sensor element 10. On this occasion, the sensor element 10 is positioned relative to the element guide portions 33 whereas the electrode holders 40 are positioned relative to the element guide portions 33 to be fitted. For this reason, the distances between the plate surfaces of the sensor element 10 and the inner wall surfaces 42 of the electrode holders 40 are kept substantially constant without large difference between individual products.

Because the front end portion 61 of each electrode fitment 60 is shaped like a U-shaped spring, the plate surfaces of the sensor element 10 and the inner wall surfaces of the electrode holders 40 are urged to go farther from each other when the electrode holders 40 are fitted to the element guide portions 33. In this condition, the retaining fitment 48 is put to press the outer circumferences of the electrode holders 40 engaged with the element guide portions 33 to keep the engagement therebetween. The front end portions 61 of the electrode fitments 60 are kept urged to abut on the electrode terminal portions 15 and 16 of the sensor element 10, so that electrical connection therebetween is stabilized. As described above, because the distances between the plate surfaces of the sensor element 10 and the inner wall surfaces 42 of the electrode holders 40 are kept substantially constant in any positions of the electrode terminal portions 15 and 16, pressure of contact with the electrode fitments 60 does not vary according to the positions of the electrode terminal portions 15 and 16.

Then, the separator 50 is made to abut on the electrode holders 40. In this condition, the protection cover 70 shown in FIG. 1 is put on the electrode holders 40 and the separator 50. After forced into the metal shell 2, the protection cover 70 is fixed by all-round laser welding so that the protrusion portions 49 of the retaining fitment 48 abut on the inner wall of the protection cover 70. As a result, the retaining fitment 48 is held in the protection cover 70, so that the electrode holders 40 retained by the retaining fitment 48 are positioned in the protection cover 70.

As described above, in the gas sensor 1 according to this embodiment, when the sensor element 10 is fixed to the metal shell 2, the widthwise opposite side ends of the sensor element 10 are guided by the groove portions 35 of the element guide portions 33 provided in the sleeve 30 to thereby align the sensor element 10 with the axial hole 31 of the sleeve 30. The electrode fitments 60 being in contact with the electrode terminal portions 15 and 16 of the sensor element 10 are positioned and held in the electrode holders 40 in which positioning can be made relative to the element guide portions 33.

As a result, the positional relation between the electrode fitments 60 and the sensor element 10 through the element guide portions 33 is kept constant without influence of differences between individual products. Accordingly, pressure of contact between the front end portions 61 of the electrode fitments 60 and the electrode terminal portions 15 and 16 of the sensor element 10 is kept so constant that electrically stable connection can be performed. The sensor element 10 is coaxially aligned with the axial hole 31 of the sleeve 30 through the element guide portions 33 and the element guide portions 30 restrains the sensor element 10 from being inclined in a direction (that is, the width direction and the thickness direction of the sensor element 10) crossing the axial direction of the axial hole 31. Accordingly, the electrode holders 40 do not come into contact with the sensor element 10 even in the case where the electrode holders 40 are fitted to the element guide portions 33. Accordingly, there is no superfluous load applied on the sensor element 10, so that the sensor element 10 can be prevented from being broken.

The lead wires 68 arranged from the external circuit are connected to the electrode fitments 60. Because the separator 50 for guiding the lead wires 68 is provided in the rear of the element guide portions 33, the lead wires 68 can be provided separately. The lead wires 68 are prevented from being entangled with one another at the time of assembling the gas sensor 1, so that it is easy to assemble the gas sensor 1 and it is possible to prevent occurrence of short-circuiting. The small diameter portions 53 each having a diameter substantially equal to the outer diameter of a corresponding lead wire 68 are further provided at an end portion of the separator 50. For this reason, the base portions 62 of the electrode fitments 60 for caulking the lead wires 68 to fix the lead wires 68 to prevent the lead wires 68 from dropping out cannot pass through the small diameter portions 53, so that the electrode fitments 60 can be prevented from dropping out of the separator 50.

Figure 11:
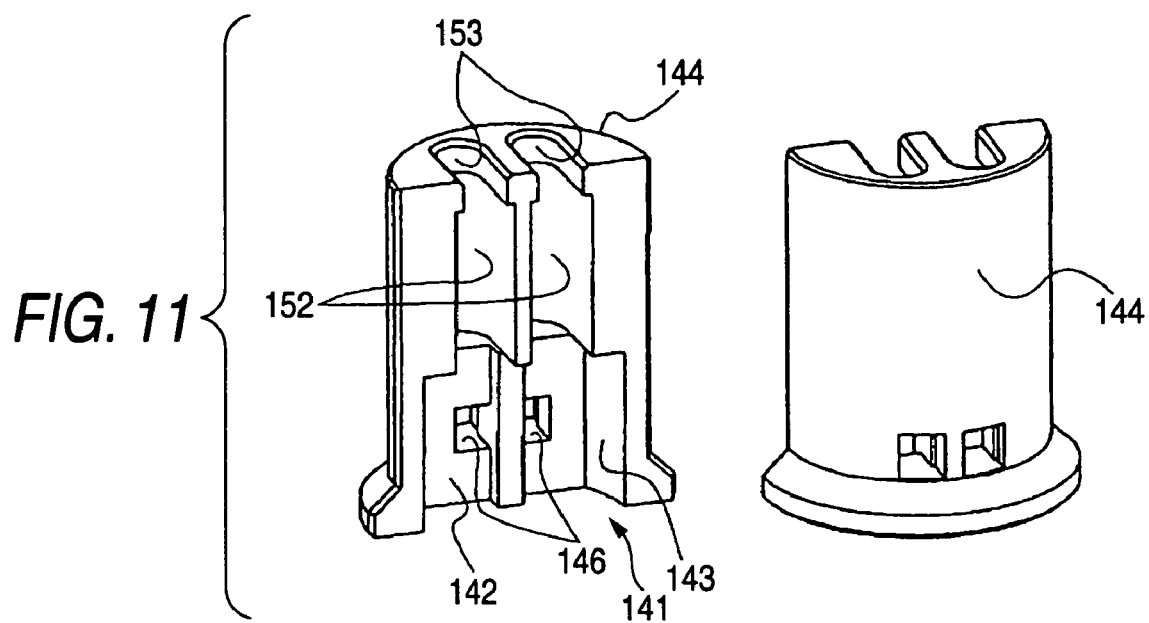
[FIG. 11] A perspective view of a pair of electrode holders 140 made of two components.

It is a matter of course that various changes may be made on the invention. For example, the aforementioned embodiment has shown the case where the electrically insulating member around the electrode fitments 60 is formed as the three components of a pair of electrode holders 40 and a separator 50. However, the electrically insulating member may be formed as two components or as one component. For example, FIG. 11 shows an example in which the electrode holders 40 and the separator 50 are integrally formed as the two components of a pair of electrode holders 140. As shown in FIG. 11, each electrode holder 140 is provided in such a manner that a portion equivalent to the separator 50 is divided vertically into two parts, and that one of the divided parts and a portion equivalent to the electrode holder 40 are integrally molded.

Each of the pair of electrode holders 140 has a concave portion 141 provided in a portion equivalent to the electrode holder 40. The concave portions 141 are formed so that the sensor element 10 together with the element guide portions 33 can be stored in the concave portions 141 when the sensor element 10 is clamped by the electrode holders 140 from the direction of the thickness of the sensor element 10. On this occasion, inner surfaces 143 of the concave portions 141 are fitted to the outer surfaces of the pair of element guide portions 33. Two openings 146 piercing each electrode holder 140 up to an outer wall surface 144 are provided in an inner wall surface 142 of the concave portion 141 facing the plate surface of the sensor element 10 in the same manner as in the electrode holder 40 according to this embodiment. The protrusion pieces 63 of the electrode fitments 60 in this embodiment are fitted into the openings 146 to thereby hold the front end portions 61 of the electrode fitments 60 in the inside of the electrode holders 140.

Two insertion grooves 152 equivalent to the through-holes 52 of the separator 50 are provided in a portion equivalent to the separator 50 of each electrode holder 140. The insertion grooves 152 are connected to the concave portion 141. Small groove width portions 153 each having a groove width substantially equal to the outer diameter of a corresponding lead wire 68 are provided at end portions of the grooves on a side opposite to the concave portion 141. The small groove width portions 153 serve as stoppers for the caulking portions 65 of the electrode fitments 60 in the same manner as in the aforementioned embodiment. When the base portions 62 of the electrode fitments 60 are stored in the insertion grooves 152 while the front end portions 61 are stored in the concave portion 141, the electrode fitments 60 are entirely stored in the electrode holders 140. Incidentally, the electrode holders 140 are equivalent to the "insulation holding members" in the scope of claim for this invention.

Figure 12:
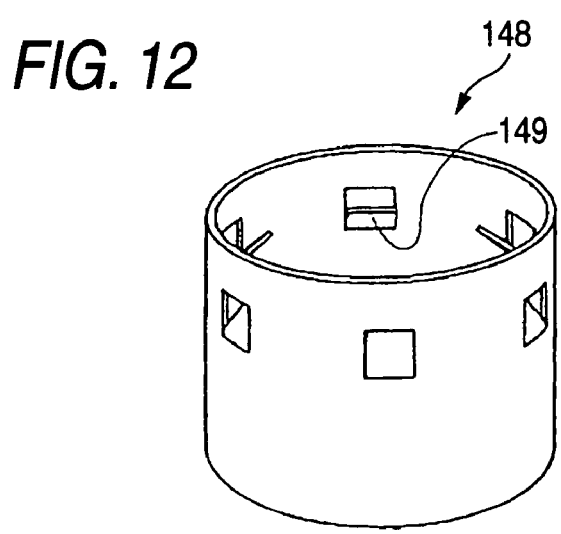
[FIG. 12] A perspective view of a retaining fitment 148 for retaining the electrode holders 140.

When the sensor element 10 together with the element guide portions 33 is clamped by the electrode holders 140, the electrode holders 140 in which the front end portions 61 of the electrode fitments 60 are positioned are fitted to the element guide portions 33. Accordingly, the positional relation between the front end portions 61 of the electrode fitments 60 and the sensor element 10 guided by the element guide portions 33 are kept substantially constant regardless of individual differences. The electrode holders 140 are held by a cylindrical retaining fitment 148 shown in FIG. 12 in the same manner as the retaining fitment 48 according to this embodiment. Protrusion portions 149 extending inward are formed at six places in the retaining fitment 148. Protrusion portions 171 (see FIG. 13) each located at the front end, extending radially inward, turning in a different direction gradually and extending to the rear end side so as to be substantially curved like a J figure are formed at six places in the retaining fitment 148.

Figure 13:
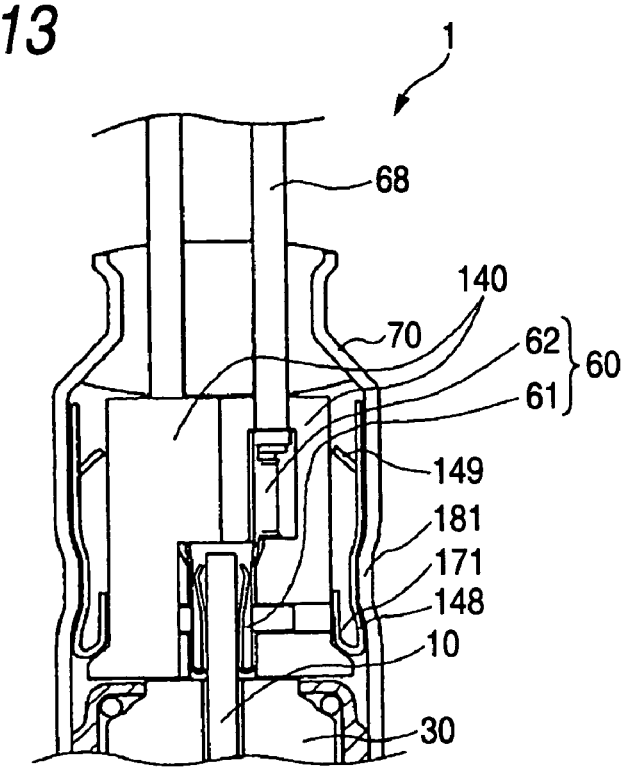
[FIG. 13] A cutaway sectional view of a main portion of the gas sensor 1 according to another embodiment in which the electrode holders 140 are combined with the sensor element 10.

As shown in FIG. 13, the retaining fitment 148 holds the electrode holders 140 in the condition that the protrusion portions 149 and the protrusion portions 171 elastically abut on the outside of the electrode holders 140 to keep the state of the sensor element 10 clamped by the pair of electrode holders 140. Moreover, the retaining fitment 148 operates so that a portion of the protection cover 70 located radially outside the retaining fitment 148 is pressed radially inward so that the retaining fitment 148 is held in the protection cover 70 in the condition that part of the retaining fitment 148 is deformed by a convex portion 181 deformed so as to be curved inward convexly.

For this reason, the electrode holders 140 are retained stably even in the case where vibration reaches the gas sensor 1. Even when external impact is further applied on the protection cover 70, the impact applied on the electrode holders 140 can be relaxed by the retaining fitment 148. Because external force transmitted to the sensor element 10 can be reduced, the element can be prevented from being broken. Alternatively, the gas sensor 1 may be formed by use of a retaining fitment having protrusion portions which are provided so as to protrude outward without provision of any convex portion 181 in the protection cover 70 as shown in the retaining fitment 48 according to the aforementioned embodiment so that the protrusion portions are made to abut on the inner wall of the protection cover 70 while the pair of electrode holders 140 are held by the inner circumference of the retaining fitment.

Figure 14:
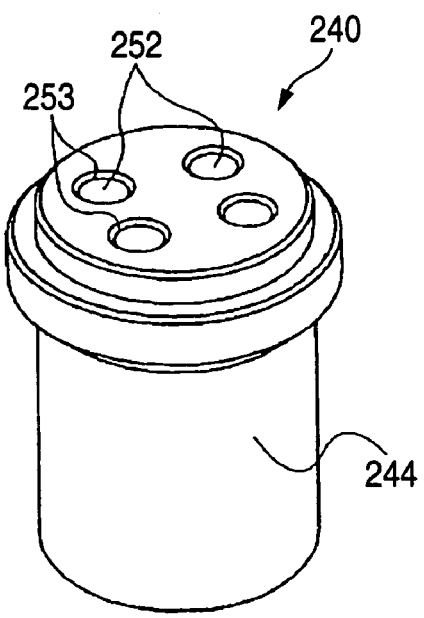
[FIG. 14] A perspective view from the rear end side, of an electrode holder 240 made of a single component.
Figure 15:
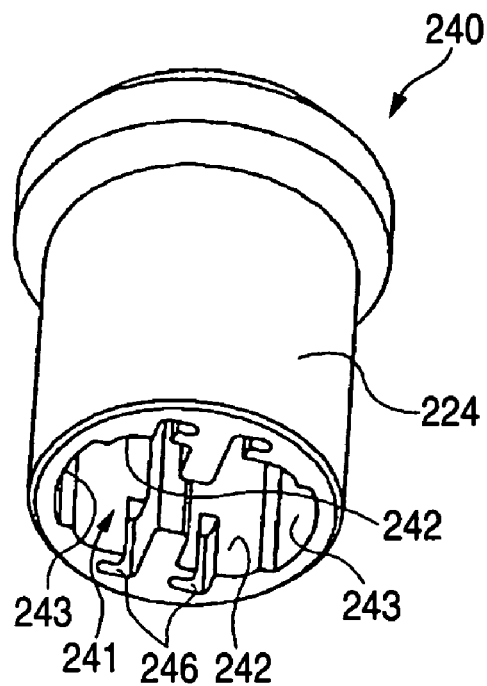
[FIG. 15] A perspective view from the front end side, of the electrode holder 240 made of a single component.

FIGS. 14 and 15 show an example in which the electrode holders 40 and the separator 50 are integrally formed into an electrode holder 240 made of a single component. The electrode holder 240 has concave portions 241 formed in portions equivalent to the electrode holders 40 so that the element guide portions 33 of the sleeve 30 can be inserted in the concave portions 241. Outer surfaces of the pair of element guide portions 33 are fitted to inner surfaces 243 of the concave portions 241 to thereby align the electrode holder 240 with the element guide portions 33.

Engagement grooves 246 each shaped like an L figure are provided at two places in each of inner wall surfaces 242 facing the plate surfaces of the sensor element 10 inserted in the concave portions 241. When the protrusion pieces 63 of the electrode fitments 60 in the aforementioned embodiment are fitted into the engagement grooves 246 while each protrusion piece 63 is shaped like an L figure in sectional view, the front end portions 61 of the electrode fitments 60 can be positioned in the concave portions 241. When the element guide portions 33 are fitted to the inner surfaces 243 of the concave portions 241, the sensor element 10 is clamped between the front end portions 61 of the electrode fitments 60 opposite to each other so that the front end portions 61 can be electrically connected to the electrode terminal portions 15 and 16. The sensor element 10 is positioned by the element guide portions 33 while the electrode holder 240 in which the front end portions 61 of the electrode fitments 60 are positioned is positioned by the element guide portions 33. For this reason, the positional relation between the front end portions 61 of the electrode fitments 60 and the sensor element 10 is kept substantially constant regardless of individual differences when the electrode holder 240 is fitted so as to be put on the element guide portions 33.

Incidentally, the point that insertion holes 252 and small diameter portions 253 are formed in a portion of the electrode holder 240 equivalent to the separator 50 and that the base portions 62 of the four electrode fitments 60 are stored therein to prevent the electrode fitments 60 from dropping out is the same as in the aforementioned embodiment. Incidentally, the electrode holder 240 is equivalent to the "insulation holding member" in the scope of claim for this invention.

Figure 16:
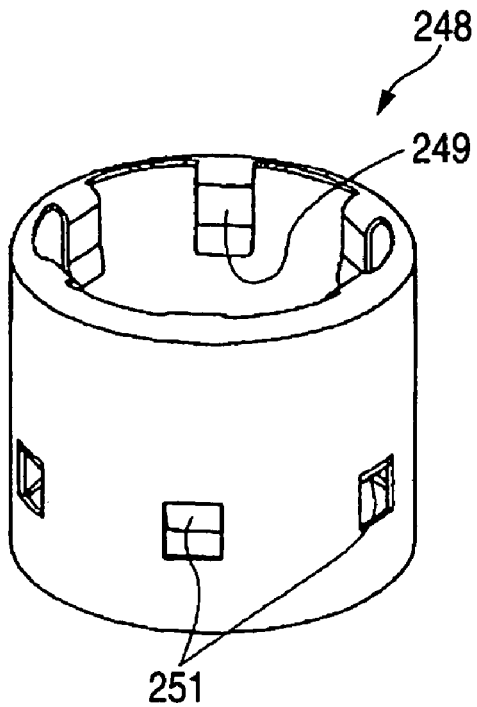
[FIG. 16] A perspective view of a retaining fitment 248 for retaining the electrode holder 240.
Figure 17:
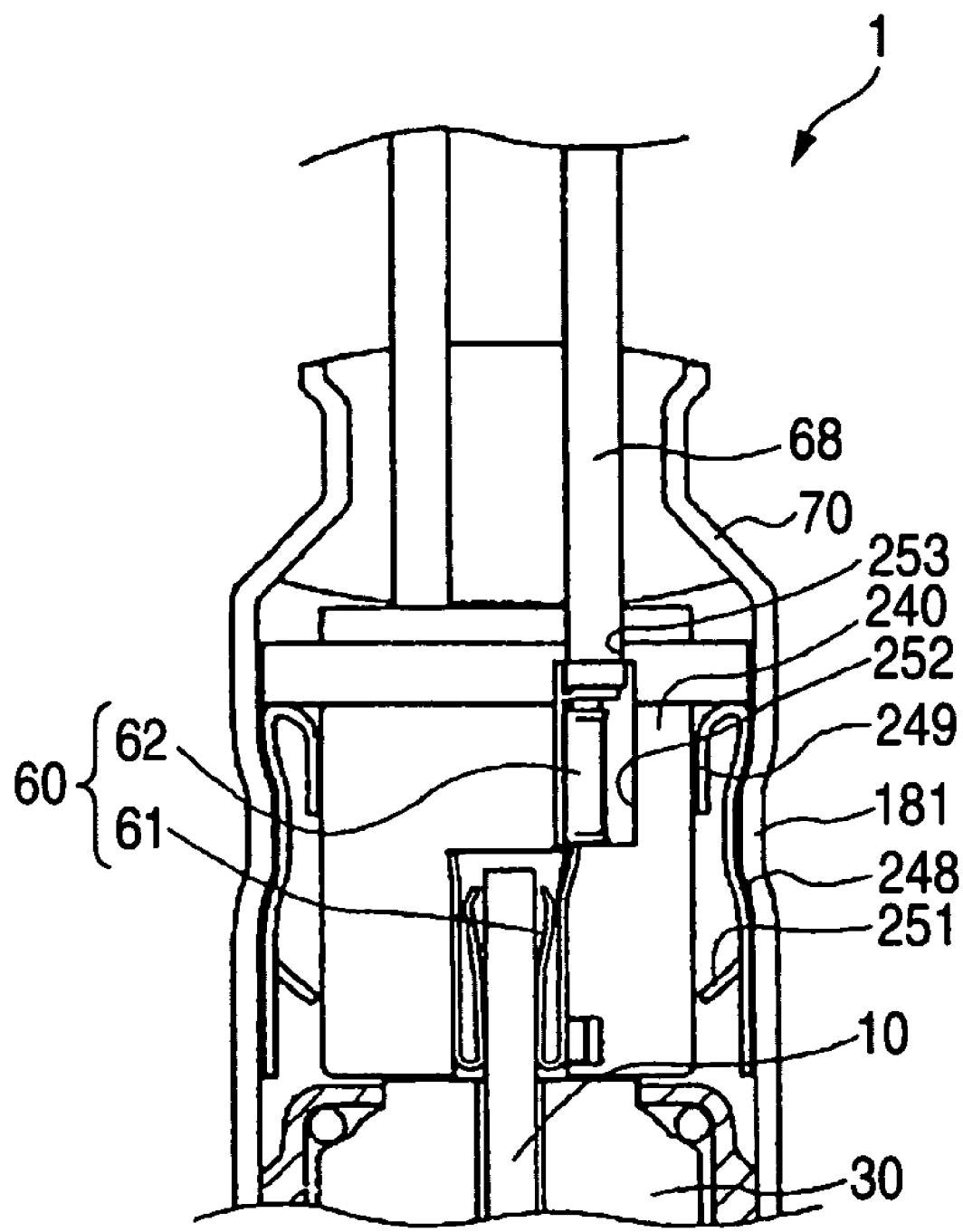
[FIG. 17] A cutaway sectional view of a main portion of the gas sensor 1 according to a further embodiment in which the electrode holder 240 is combined with the sensor element 10.

The electrode holder 240 is retained in the protection cover 70 by a cylindrical retaining fitment 248 shown in FIG. 16. Protrusion portions 251 extending inward are formed at six places in the retaining fitment 248. Protrusion portions 249 each located at the rear end, extending radially inward, turning in a different direction gradually and extending to the front end side so as to be substantially curved like a J figure are formed at six places in the retaining fitment 148. As shown in FIG. 17, the retaining fitment 248 holds the electrode holder 240 in the condition that the protrusion portions 249 and the protrusion portions 251 elastically abut on the outside of the electrode holder 240. Moreover, the retaining fitment 248 operates so that a portion of the protection cover 70 located radially outside the retaining fitment 248 is pressed radially inward so that the retaining fitment 248 is held in the protection cover 70 in the condition that part of the retaining fitment 248 is deformed by the convex portion 181 deformed so as to be curved inward convexly.

For this reason, the electrode holder 240 is retained stably even in the case where vibration reaches the gas sensor 1. Even when external impact is further applied on the protection cover 70, the impact applied on the electrode holder 240 can be relaxed by the retaining fitment 248. Alternatively, the gas sensor 1 may be formed by use of a retaining fitment having protrusion portions which are provided so as to protrude outward without provision of any convex portion 181 in the protection cover 70 as shown in the retaining fitment 48 according to the aforementioned embodiment so that the protrusion portions are made to abut on the inner wall of the protection cover 70 while the electrode holder 240 is held by the inner circumference of the retaining fitment.

Although the aforementioned embodiment has shown the case where element guide portions 33 making a pair are provided while groove portions 35 for guiding widthwise opposite side ends of the sensor element 10 are provided, the configuration of the element guide portions 33 is not limited thereto. The element guide portions 33 may be formed as four guide members for guiding ridge lines of four corners of the sensor element 10. Although the front end portion 61 of each electrode fitment 60 is shaped like a U-shaped spring, the front end portion 61 may be shaped like a plate spring or a wavy spring having urging force in a direction perpendicular to the inner wall surface 42 of the electrode holder 40 so that the front end portion 61 can be positioned and held in the inner wall surface 42.

Although the invention has been described in detail or with reference to specific embodiments, it will be obvious to those skilled in the art that various changes and modifications may be made without departing from the spirit and scope of the invention.

This application is based on Japanese Patent Application (Patent Application No. 2004-079813) filed on Mar. 19, 2004 and the contents thereof are incorporated herein by reference.

INDUSTRIAL APPLICABILITY

Although the aforementioned embodiments have shown the case where an oxygen sensor is provided as a gas sensor to which the invention can be applied, the invention can be also applied to various kinds of gas sensors with plate-like sensor elements such as a total environment air-fuel ratio sensor, an NOx sensor, etc.

The invention claimed is:

1. A gas sensor comprising:
   a cylindrical metal shell;
   a plate-like sensor element extending in a lengthwise direction and including a front end side exposed to gas to be measured and electrode terminal portions formed on upper and lower surfaces on a rear end side so as to come into contact with connection terminals; and
   a sleeve held in an inside of the metal shell and including an axial hole in which the sensor element is inserted,
   wherein the sleeve further includes element guide portions which protrude from an opening end surface on a rear end side of the axial hole and which restrain the sensor element from being inclined in a direction crossing an axial direction of the axial hole, and
   wherein the sleeve includes a pair of element guide portions which are arranged opposite to each other with respect to a center axial line of the axial hole, so that at least part of the electrode terminal portions of the sensor element are exposed at a gap between the pair of element guide portions.

2. The gas sensor as claimed in claim 1, wherein the pair of element guide portions have groove portions continuously provided in an inner circumference of the axial hole so that at least one of widthwise opposite side ends of the sensor element is stored in the groove portions.

3. The gas sensor as claimed in claim 1, wherein:
   insulation holding members are provided around a rear end side of the sensor element, and the connection terminals are provided between the sensor element and the insulation holding members so as to come into contact with the electrode terminal portions; and
   inner surfaces of the insulation holding members are fitted to outer surfaces of the element guide portions.

4. The gas sensor as claimed in claim 3, wherein the insulation holding members make a pair and clamp and fix the connection terminals and the sensor element.

5. The gas sensor as claimed in claim 4, further comprising:
   a protection cover fixed to the metal shell so as to surround the insulation holding members; and
   a retaining fitment which is shaped like a pipe surrounding outer circumferences of the insulation holding members and which is held in an inside of the protection cover while the connection terminals and the sensor element are kept clamped by the insulation holding members.

6. The gas sensor as claimed in claim 3, wherein the insulation holding members are replaced by a single member which is provided for covering the rear end side surroundings of the sensor element and which has though-holes on a rear end side so that lead wires connected to the connection terminals are inserted in the through-holes.

7. The gas sensor as claimed in claim 6, further comprising:
   a protection cover fixed to the metal shell so as to surround the insulation holding member; and
   a retaining fitment which is held in an inside of the protection cover while the insulation holding member is held in an inside of the retaining fitment.

8. A gas sensor comprising:
   a cylindrical metal shell;
   a plate-like sensor element extending in a lengthwise direction and including a front end side exposed to gas to be measured and electrode terminal portions formed on a rear end side so as to come into contact with connection terminals; and
   a sleeve held in the inside of the metal shell and including an axial hole in which the sensor element is inserted,
   wherein the sleeve further includes element guide portions which protrude from an opening end surface on a rear end side of the axial hole and which guide the rear end side of the sensor element coaxially with the axial hole, and
   wherein the sleeve includes a pair of element guide portions which are arranged opposite to each other with respect to a center axial line of the axial hole, so that at least part of the electrode terminal portions of the sensor element are exposed at a gap between the pair of element guide portions.

9. A gas sensor comprising:
   a cylindrical metal shell;
   a plate-like sensor element extending in a lengthwise direction and including a front end side exposed to gas to be measured and electrode terminal portions formed on upper and lower surfaces on a rear end side so as to come into contact with connection terminals; and
   a sleeve held in an inside of the metal shell and including an axial hole in which the sensor element is inserted, wherein
   the sleeve further includes element guide portions which protrude from an opening end surface on a rear end side of the axial hole and which restrain the sensor element from being inclined in a direction crossing an axial direction of the axial hole,
   insulation holding members are provided around a rear end side of the sensor element, and the connection terminals are provided between the sensor element and the insulation holding members so as to come into contact with the electrode terminal portions, and
   inner surfaces of the insulation holding members are fitted to outer surfaces of the element guide portions.

10. A gas sensor comprising:
    a cylindrical metal shell;
    a plate-like sensor element extending in a lengthwise direction and including a front end side exposed to gas to be measured and electrode terminal portions formed on a rear end side so as to come into contact with connection terminals; and
    a sleeve held in the inside of the metal shell and including an axial hole in which the sensor element is inserted, wherein
    the sleeve further includes element guide portions which protrude from an opening end surface on a rear end side of the axial hole and which restrain the sensor element from being inclined in a direction crossing an axial direction of the axial hole,
    insulation holding members are provided around a rear end side of the sensor element, and the connection terminals are provided between the sensor element and the insulation holding members so as to come into contact with the electrode terminal portions, and
    inner surfaces of the insulation holding members are fitted to outer surfaces of the element guide portions.

* * * * *